US005777084A

United States Patent [19]

Buhring

[11] Patent Number: 5,777,084
[45] Date of Patent: Jul. 7, 1998

[54] ANTIBODY BV10A4H2 SPECIFIC FOR HUMAN FLT3/FLK2 RECEPTOR AND MYBRIDOMA

[75] Inventor: Hans-Jorg Buhring, Tübingen, Germany

[73] Assignee: Eberhard-Karls-Universität Tübingen, Tübingen, Germany

[21] Appl. No.: 792,626

[22] Filed: Jan. 31, 1997

[30] Foreign Application Priority Data

Mar. 7, 1996 [DE] Germany ............... 196 08 769.4

[51] Int. Cl.$^6$ ............................................. A61K 39/395
[52] U.S. Cl. ..................... 530/388.22; 530/388.73; 435/334; 435/343.1; 435/172.3; 424/143.1; 424/144.1
[58] Field of Search ............... 530/387.7, 388.22, 530/388.73; 435/334, 343.1, 172.2; 424/143.1, 144.1

[56] References Cited

U.S. PATENT DOCUMENTS 5,376,531  12/1994  Anderson et al. ................ 435/7.23

OTHER PUBLICATIONS

1) Osband, ME et al. Immunol. Today 11: 193–195, 1990.
2) Rosnet, O. et al. Leukemia, 10: 238–248, 1996.
3) Rose C. et al. Hybridoma 14(5): 453–459, 1995.
4) Lyman SD et al. Oncogene 8(4): 815–822, 1993.
5) Meierhoff, G. et al. Leukemia, 9: 1368–1372, 1995.
6) Schlom J. In: Mol. Foundation Oncology, S. Broder (ed.) pp. 95–134, 1991.
Bennett, J.M. et al., "Proposed Revised Criteria for the Classification of Acute Myeloid Leukemia"; *Annals of Internal Medicine*, vol. 103 No. 4, pp. 620–625 (1985).
Buhring, H.J. et al., "The Monoclonal Antibody 11G7 Recognizes a Novel Differentiation Antigen Expressed on Hemopoietic Precursor Cells", *Hybridoma*, vol. 10 No. 1; pp. 77–88 (1991).
Buhring, H.J. et. al., "Modulation of p145$^{c-kit}$ Function in Cells of Patients with Acute Myeloblastic Leukemia$^1$", *Cancer Research* 53, pp. 4424–4431 (1993).

Hannun, C. et al., "Ligand for FLT3/FLK2 Receptor Tyrosine Kinase Regulates Growth of Haematopoietic Stem Cells and is Encoded by Variant RNAs", *Letters to Nature*, vol. 368, pp. 643–648 (1994).
Hirayama, F. et al., "The flt3 Ligand Supports Proliferation of Lymphohematopoietic Progenitors and Early B-Lymphoid Progenitors", *Blood*, vol. 85 No. 7, pp. 1762–1768 (1995).
Lyman, S.D. et al., Cloning of the Human Homologue of the Murine flt3 Ligand: A Growth Factor for Early Hematopoietic Progenitor Cells, *Blood*, vol. 83 No. 10, pp. 2795–2801 (1994).
Matthews, Wm. et al., "Receptor Tyrosine Kinase Specific to Hematopoietic Stem and Progenitor Cell–Enriched Populations", *Cell*, vol. 65, pp. 1143–1152 (1991).
Muench, M.O. et al., "FLK-2/FLT-3 Ligand Regulates the Growth of Early Myeloid Progenitors Isolated From Human Fetal Liver", *Blood*, vol. 85 No. 4, pp. 963–972 (1995).
Rosnert O. et al., "Human FLT3/FLK2 Receptor Tyrosine Kinase is Expressed at the Surface of Normal and Malignant Hematopoietic Cells", *Leukemia*, vol. 10, pp. 238–248 (1996).
Small, D. et al., "STK-1, the Human Homolog of Flk-2/Flt-3, is Selectively Expressed in DC43$^+$ Human Bone Marrow Cells and Is Involved in the Proliferation of Early Progenitor/Stem Cells", *Pro. Natl. Acad. Sci. USA*, vol. 91, pp. 459–463 (1994).

*Primary Examiner*—Sheela Huff
*Assistant Examiner*—Julie E. Reeves
*Attorney, Agent, or Firm*—Oppenheimer W. Donnelly; Claude A. S. Hamrick

[57] ABSTRACT

The invention relates to a monoclonal antibody specifically binding to the human FLT3/FLK2 receptor protein. The invention further relates to hybridoma cells producing such an antibody, as well as to a method for generation of such hybridoma cells. One example of such a monoclonal antibody is the antibody produced and released by hybridoma cells deposited under No. DSM 2248 at the German Collection of Microorganisms and Cell Cultures (DSMZ).

2 Claims, 2 Drawing Sheets

ANTIBODY BV10A4H2 SPECIFIC FOR HUMAN FLT3/FLK2 RECEPTOR AND MYBRIDOMA

BACKGROUND OF THE INVENTION

1. Field of the Invention

The invention relates to a monoclonal antibody directed against the human tyrosine kinase receptor FLT3/FLK2.

The tyrosine kinase receptor FLT3/FLK2 plays an important role in early hematopoiesis. It naturally occurs in blood stem cells and early lymphoid and myeloid blood progenitor cells and interacts with a growth factor FLT3-ligand (FL), that particularly stimulates the recruitment and proliferation of these cells (Matthews et al., Cell 65:1143, 1991; Small et al., Proc. Natl. Acad. Sci. USA 91:459, 1994; Lyman et al., Blood 83:2795, 1994; Muench et al., Blood 85:963, 1995; Hannum et al., Nature 368:643, 1994; Hirayama et al., Blood 85:1762, 1995).

2. Description of the Related Art

The indirect detection mediated by an antibody specifically binding to the receptor represents a safe and quick method to qualitatively and quantitatively detect membrane bound receptors. The specific antibody can be labeled either directly or indirectly, using the label for identification and quantitative determination of the antibody or the bound receptor, respectively. Particularly fluorescent dyes or radioactive agents can be used as labels.

Such an antibody can also be coupled to a special therapeutically active agent and therefore renders possible a targeted cellular treatment, which is particularly required for the treatment of tumorous illnesses.

Antibodies directed against FLT3/FLK2 receptor protein have been described previously, however, these antibodies are directed against the murine FLT3/FLK2 receptor protein. Therefore, lacking the required specificity, these antibodies are not suitable for the treatment of human cells.

SUMMARY OF THE INVENTION

It is therefore an object of the present invention to provide an antibody specifically binding to the native unmodified human FLT3/FLK2 receptor protein and which is available in practically unlimited amounts.

This object is achieved by providing a monoclonal antibody binding specifically to the native unmodified human FLT3/FLK2 receptor protein. Such a monoclonal antibody is produced and released by hybridoma cells that were deposited on Dec. 19, 1995, under No. DSM ACC2248 at the German Collection of Microorganisms and Cell Cultures Ltd. (DSMZ) in accordance with the Budapest Treaty. The antibody has been given the designation BV10A4H2.

With the antibody according to the invention, a monoclonal antibody has been provided for the first time that is reproduceable in a standardized manner and can thus potentially be produced in unlimited amounts and that binds specifically to a respective special extracellular epitope of the human receptor protein FLT3/FLK2.

The antibody according to the invention permits a targeted detection and modulation of cells comprising an extracellular domain of the human FLT3/FLK2 receptor protein. It therefore provides to physicians and research personnel a sofar unique and variably applicable means for on the one hand detecting such cells, both in cell culture and in the patient's organism, and on the other hand manipulating such cells, if desired, either by means of the antibody as such, or by specific reagents coupled to it.

The invention further relates to hybridoma cells producing a monoclonal antibody directed against the FLT3/FLK2 receptor protein. It comprises particularly the hybridoma cells deposited at the International Depository DSMZ-Deutsche Sammlung Von Mikroorganismen Und Sellkulturen Gmbh (German Collection of Microorganisms and Cell Cultures, Ltd. (DSMZ)), Mascheroder Weg 1b, D-38124 Braunschweig Germany under the number DSM ACC2248 at the German Collection of Microorganisms and Cell Cultures Ltd. (DSMZ) according to the Budapest Treaty and producing the antibody designated BV10A4H2.

The invention further relates to a method for producing hybridoma cells synthesizing and releasing an antibody directed against the native unmodified FLT3/FLK2 receptor protein. This method comprises the steps generally known in the art, as described for example by Bühring et al. in Hybridoma 1991, Vol. 10, No. 1, pp. 77–78:

1. Immunizing or sensitization of an animal, preferably a mouse of the Balb/c line, with the antigen or immunogen;
2. collecting the antibody-producing cells, preferably the lymphocytes of the spleen of that animal;
3. fusion of these antibody-producing cells with a stable, immortalized cell line, preferably a myeloma cell line, to hybridoma cells; and
4. isolation and multiplication (cloning) of such hybridoma cells that secrete an antibody binding to the antigen.

The method according to the invention is characterized by the fact that the animal is immunized with cells of the hematopoietic pre-B cell line BV-173, freely available at the DSMZ under No. DSM ACC20.

It is advantageous that the cells of this pro-B cell line BV-173 present a strong expression of FLT3/FLK2 receptor protein, as has been shown during the experiments leading to the antibody BV10A4H2.

When screening hybridoma cells producing antibodies specific for FLT3/FLK2 receptor protein, it is preferred, if only those isolated and cloned hybridoma cells are selected which produce antibodies having a specificity for the cells of the murine cell line BA/F3, previously transfected with the complete DNA-sequence for the human FLT3/FLK2 (BA/F3-huFLT3).

The invention also relates to the use of a monoclonal antibody directed against the FLT3/FLK2 receptor protein for diagnostic and/or therapeutic treatment of tumors, particularly of malignant hematopoietic cells as for example lymphoid and myeloid leukemia cells.

Surprisingly, it has been found that most malignant hematopoietic cells as, for example, lymphoid and myeloid leukemia cells comprise a comparably high content of FLT3/FLK2 receptor protein. An antibody according to the invention coupled to a means for detection, for instance a radioactive marker, indirectly binds this detection means to the respective cells and thus allows the direct detection of the cells, for example using x-ray diagnostic/scintigraphic methods. Therefore, a very early diagnosis of tumors is possible, even in vivo.

In an analogous way the antibody may be coupled to therapeutically active agents and therefore allows a direct and targeted modulation or even elimination of FLT3/FLK2 receptor protein carrying cells, particularly leukemia cells.

In a preferred embodiment the antibody produced and released by the hybridoma cells deposited under No. DSM ACC2248 at the German Collection of Microorganisms and Cell Cultures Ltd. (DSMZ) is being used for such a diagnostic and/or therapeutic treatment.

In order to facilitate the therapeutic and/or diagnostic application of the antibody according to the invention, the antibody may be mixed in a pharmaceutical composition with adequate accessory substances. Consequently, the invention also relates to a pharmaceutical agent for diagnostic and/or therapeutic treatment of tumors, comprising an antibody binding to human FLT3/FLK2 receptor protein according to the invention. Preferably, this pharmaceutical agent comprises an antibody produced and released by the hybridoma cells deposited under No. DSM ACC2248 at the German Collection of Microorganisms and Cell Cultures Ltd. (DSMZ).

Using an antibody according to the invention, cells carrying the human FLT3/FLK2 receptor protein may be detected in a suspension of different (human) cells using the methods known in the art, for instance the enzyme-linked immunosorbent assay, ELISA, or the radio immuno assay, RIA. The present invention therefore also relates to a kit for the detection of human FLT3/FLK2 receptor protein, comprising a monoclonal antibody specifically binding to the native human FLT3/FLK2 receptor protein.

A preferred embodiment of this kit is characterized by the fact that the kit comprises an antibody generated by the hybridoma cells deposited under No. DSM ACC2248 at the German Collection of Microorganisms and Cell Cultures Ltd. (DSMZ).

In connection with the present invention, it has surprisingly been found that the monoclonal antibody designated BV10A4H2, generated by the hybridoma cells deposited under No. DSM ACC2248 at the German Collection of Microorganisms and Cell Cultures Ltd. (DSMZ) binds to human stem cells.

The invention therefore also relates to the use of an antibody according to the invention, preferably of the antibody BV10A4H2, for detection of hematopoietic cells, as well as to a kit for the detection of hematopoietic cells, comprising an antibody according to the invention, preferably the antibody BV10A4H2. It is thereby possible to separate undifferentiated CD34$^+$ subpopulations and to select and purify cells from bone marrow for functional analyses.

Further advantages can be taken from the following description.

It is understood that the afore-mentioned features and those to be explained below can be used not only in the specific combinations, but also in other combinations or alone without going beyond the scope of the present invention.

DETAILED DESCRIPTION OF THE EMBODIMENTS OF THE INVENTION

EXAMPLE 1

Figures 1A, 1B:
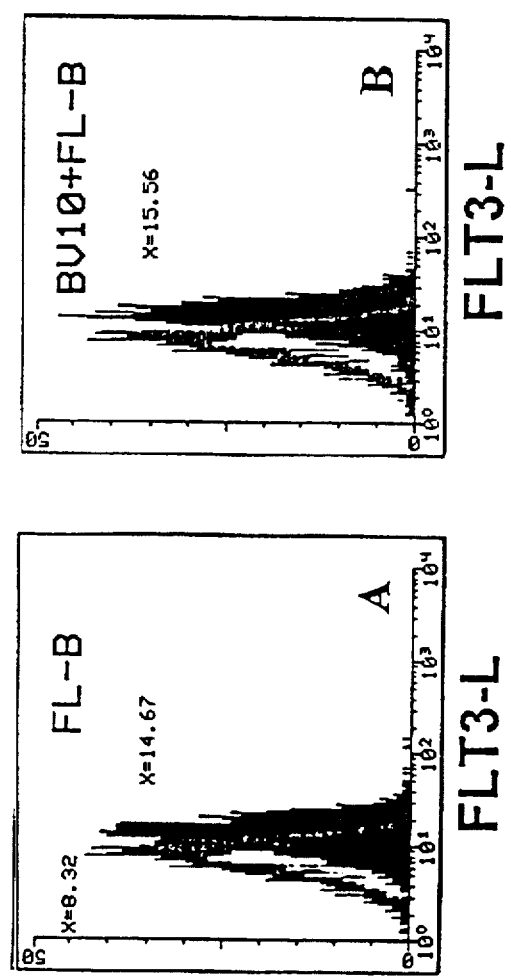
FIG. 1A shows a histogram of a flow cytometer measurement of 4G1 cells incubated with ligand and without antibody.
FIG. 1B shows a histogram of a flow cytometer measurement of 4G1 cells incubated with ligand and antibody BV10A4H2 (therein designated BV10)

Generation and characterization of monoclonal antibodies directed against the FLT3/FLK2 receptor protein Cells of the hematopoietic pre-B cell line BV-173 (DSM ACC20) are used as an antigen.

Eight weeks old Balb/c mice are immunized intraperitoneally twice, at intervals of 10 days, with $10^7$ cells of the cell line BV-173. Four days before the fusion, $5 \times 10^5$ cells are administered directly into the spleen in order to reinforce the immune response.

The formation of antibodies in the organism of the mouse is tested by screening the blood serum of the respective animal for binding properties with the antigen using the ELISA test well-known to any person skilled in the art.

Approximately 3 weeks later the lymphocytes of the successfully immunized animal are collected by removing the animal's spleen and disintegrating it into a cell suspension.

The suspended spleen cells are fused with myeloma cells of the known cell line SP2/0 in the presence of polyethylene glycol. The fusion culture is cultivated in a medium containing hypoxanthine, aminopterine and thymidine (HAT), herein HAT-RPMI-1640, in which only hybrid cells grow as these have both the property of myeloma cells to divide infinitely, and the property of the antibody-producing lymphocytes to grow in a medium containing HAT.

Following fusion, the cells are plated into microtiter plates and are incubated at 37° C. in the presence of 5% $CO_2$.

The culture supernatants are screened in a flow cytometer after 10–14 days on cells of the mouse cell line BA/F3, previously transfected with the complete cDNA sequence for the human FLT3/FLK2 receptor (BA/F3-huFLT3).

To generate these BA/F3-huFLT3 cells the complete coding sequence of the human cDNA for FLT3/FLK2 receptor protein was cloned into the mammalian expression vector pCD-SRα and introduced together with a plasmid conferring G418 resistance into the interleukin-3 dependent BA/F3 cells.

Transfected cells expressing the FLT3/FLK2 receptor were isolated and concentrated on the basis of their G418 resistance and according to their growth in the presence of recombinant FLT3/FLK2 receptor protein-ligand (FL) (Lyman et al., Cell 75:1157, 1993). One clone, 4G1, was selected after limited dilution and tested for its ability to express FLT3/FLK2 receptor protein. For this purpose cells of clone 4G1 were first labeled with radioactive methionine ($^{35}$S) and then incubated with a rabbit antiserum directed against the inserted domain of the tyrosine kinase of the receptor protein FLT3/FLK2. The thus generated immunoprecipitate was analyzed using polyacrylamide gel electrophoresis.

The thus reconfirmed BA/F3-HuFLT3 cells of the clone 4G1 were used as the antigen in the screening procedure.

In a subsequent step the supernatants were tested for reactivity with the cells of the cell line BA/F3, as these cells do not express antigens.

Hybridoma cells producing antibodies specific for 4G1 cells are selected, isolated and cultivated, i.e. cloned, according to the known limited dilution method.

Positively reacting hybridoma cell cultures are subjected to further cultivation, the antibodies are concentrated, purified and characterized.

The monoclonal antibody BV10A4H2 was obtained using the above-mentioned screening strategy. Using a phycoerythrine (PE)-conjugated anti-isotype-specific antiserum by direct immuno-fluorescence using flow cytometry, the isotype IgG1 was determined.

Production, purification and characterization of the antibodies were carried out using methods generally known in the art.

The antibody BV10A4H2 produced by the hybridoma cells deposited under No. DSM ACC2248 at the German Collection of Microorganisms and Cell Cultures Ltd. (DSM), exhibits the following characteristic features:
Immunoglobulin class: IgG1
specific binding affinity to: human FLT3/FLK2 receptor protein (extracellular domain)

EXAMPLE 2

Identification of the antigen recognized by the monoclonal antibody BV10A4H2.

Identification of the antigen was carried out by testing binding to cells with and without FLT3/FLK2 receptor.

A sample (A) containing mouse fibroblasts of the cell line BA/F3-huFLT3 generated according to example 1 and transfected with the human cDNA for FLT3/FLK2 receptor, was incubated with the antibody BV10A4H2 of the invention.

As a control, sample (B) containing mouse fibroblasts of non-transfected cell line BA/F3 was equally incubated with the antibody BV10A4H2 in the same concentration as sample (A).

Both samples were labeled with an anti-IgG1-PE antiserum and then analyzed in a flow cytometer.

Binding of the antibody BV10A4H2 could be shown exclusively for sample (A). This means that the antibody BV10A4H2 according to the invention had specifically bound to those cells transformed with the cDNA for human FLT3/FLK2 receptor and therefore expressing the human FLT3/FLK2 receptor.

EXAMPLE 3

Identification of the monoclonal antibody BV10A4H2 as a non-antagonistic and slightly agonistic reacting antibody In tyrosine kinase receptors such as the FLT3/FLK2 receptor receptor activation initiated by ligand binding first leads to formation of receptor dimer complexes and internalization into the cell. Some antibodies can simulate the ligand, i.e. they act agonistically, and therefore lead to such a receptor dimer formation and internalization as well (Bühring et al., Cancer Res.53: 4424, 1993).

A sample (A) containing 4G1 cells (obtained according to example 1) was incubated with 200 ng/ml biotinylated FLT3 ligand-biotine and streptavidin-phycoerythrine (SA-PE).

A second sample containing 4G1 cells (B) was initially incubated with 7 µg/ml of the antibody BV10A4H2 for 30 minutes and subsequently treated as sample (1A).

Both samples were analyzed in the flow cytometer. The resulting histograms are given in FIG. 1.

Both histograms show equally strong signals. This means that the antibody BV10A4H2 according to the invention has no inhibiting effect to the ligand binding and therefore does not act antagonistically (Bühring et al., Cancer Res. 53: 4424, 1993).

For detection of the agonistic reaction sample (B) containing cells of the hematopoietic pro-B cell line BV-173 (DSM ACC 20; freely accessible) was preincubated with a control IgG1 antibody for 2 hours at 37° C., then incubated with the antibody BV10A4H2 of the invention and finally incubated with the anti-IgG1-PE antiserum.

Another sample (C) was initially incubated with the antibody BV10A4H2 and subsequently treated as sample (B).

A control sample (A) was initially incubated with 100 ng/ml FLT3/FLK2 receptor ligand and then treated as sample (B).

Figures 2A, 2B, 2C:
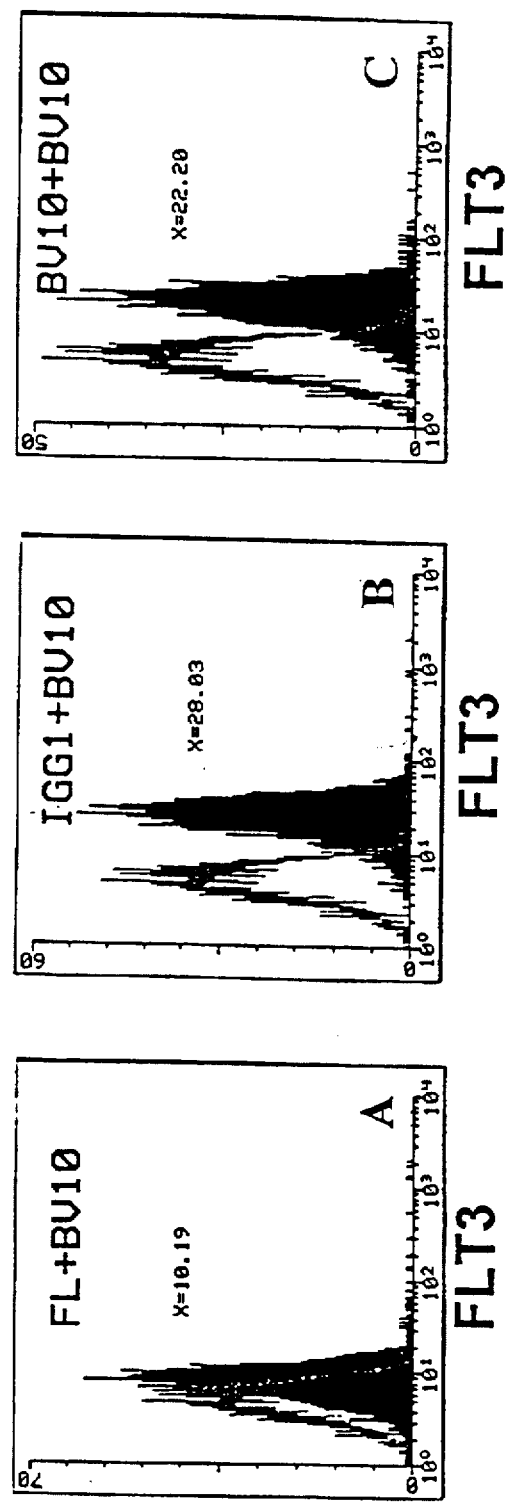
FIG. 2A shows a histogram of a flow cytometer measurement on BV-173 cells incubated with ligand alone.
FIG. 2B shows a histogram of flow cytometer measurements on BV-173 cells pre-incubated with the control antibody and then incubated with the antibody BV10A4H2 (therein designated BV10) and the ligand.
FIG. 2C shows a flow cytometer measurement on BV-173 cells pre-incubated directly with the antibody BV10A4H2 (therein designated BV10) according to the present invention and with the ligand.

The three samples were analyzed in the flow cytometer. The resulting histograms are given in FIG. 2. Compared to histogram B histogram C shows a signal reduced by approximately 33%. This means that the antibody BV10A4H2 according to the invention caused internalization of some FLT3/FLK2 receptors and therefore acts slightly in an agonistic way (ligand stimulating).

Compared to histogram B histogram A shows a signal reduced by 90% caused by internalization of the FLT3/FLK2 receptors by naturally occurring ligands.

EXAMPLE 4

Use of the monoclonal antibody BV10A4H2 for detection of subpopulations of blood stem cells A sample containing freshly obtained bone marrow cells was separated in a Ficoll-Hypaque density gradient and the normal, mononuclear bone marrow cells were isolated and concentrated.

These mononuclear bone marrow cells were then incubated with a PE-conjugate of the antibody BV10A4H2 of the invention and with known fluorescein-isothiocyanate (FITC)-conjugated antibodies directed against the stem cell antigens HLA-DR, CD34 and CD62L, respectively, CD33 occurring in myeloid cells, CD71 occurring in erythroid and progenitor cells, CD10 and CD19 occurring in B-cells, respectively and CD3 and CD7, occurring in T-cells, respectively.

The cells were analyzed in a flow cytometer.

The results of the analysis show:

a strong co-expression of FLT3/FLK2 with the stem cell markers CD34, HLA-DR and CD62L (55% and 100% and 60%, respectively), a weaker co-expression of the myeloid cell marker CD33 and the erythroid and progenitor cell markers CD10 and CD19 (60% and 20% and 20%, respectively), and no co-expression with the T-cell markers CD7 and CD3.

This means that blood stem cells as well as myeloid cells and progenitor cells of the B-line can be identified and particularly differentiated from T-cells using the antibody BV10A4H2 of the invention.

A 3-color analysis was carried out for characterization of subpopulations of the CD34$^+$ stem cell population as follows:

The mononuclear cells were incubated with a PE-conjugate of the antibody BV10A4H2 of the invention, with the known FITC-conjugated antibody directed against CD34, and a known biotine-conjugated antibody directed against CD117, and subsequently analyzed in the flow cytometer.

The obtained results show that 23% of the CD34$^+$ cells also express the receptor protein FLT3/FLK2 and 50% of the cells of this subpopulation additionally comprise the protein CD117.

Analyses on CD34$^{++}$ and CD34$^{+++}$ cells show that the number of cells of the subpopulation of FLT3/FLK2$^+$/CD117$^+$ cells decreases when CD34 expression is decreasing (from CD34$^{+++}$ via CD34$^{++}$ up to CD34$^+$), while the subpopulation of FLT3/FLK2$^+$/CD117$^-$ cells is increasing.

It is therefore possible to isolate two new subpopulations of the CD 34-positive population of blood stem cells using the antibody BV10A4H2 of the invention, namely the subpopulation FLT3/FLK2$^+$/CD117$^+$ and the subpopulation FLT3/FLK2$^+$/CD117$^-$.

EXAMPLE 5

Use of the monoclonal antibody BV10A4H2 for detection of leukemic blasts of the myeloid and B-lymphocytic line By centrifugation in a Ficoll gradient, a pure (>90%) population of leukemic blasts was obtained from bone marrow or peripheral blood of patients suffering from leukemia.

The cells were classified according to the French-American-British (FAB) classification (Bennet et al., Ann. Intern. Med. 103: 620, 1985) and this classification was confirmed by phenotypic analyses.

The cells were incubated with the antibody BV10A4H2, the bound antibody was labeled with the PE-conjugated anti-IgG1 antiserum and the cells were analyzed in the flow cytometer.

In most of the blast-populations of patients suffering from acute myeloid and/or B-lymphocytic leukemia a positive reaction and therefore the presence of FLT3/FLK2 receptor protein was detected.

Further to these analyses using freshly isolated leukemia cells, samples of megakaryoblastic cell lines, myeloid/monocytic cell lines, and B-cell lines were tested.

The cells of all samples were equally incubated with the antibody BV10A4H2, the bound antibody was labeled with a PE-conjugated anti-IgG1 antiserum and the cells were analyzed in the flow cytometer.

A positive reaction and therefore an expression of FLT3/FLK2 receptor protein was found on most of the cell lines of the B-lymphocytic line, and on few of the myeloid line.

The antibody BV10A4H2 of the invention has therefore proven to be a particularly well-suited means for the detection and identification of malignant hematopoietic cells of the myeloid and B-lymphocytic line.

What I claim, is:

1. A monoclonal antibody that binds specifically to the human FLT3/FLK2 receptor protein, wherein the antibody is produced and released by hybridoma cells that were deposited on Dec. 19, 1995 under No. DSM ACC2248 at the German Collection of Microorganisms and Cell Cultures Ltd. (DSMZ) in accordance with the Budapest Treaty, and designated BV10A4H2.

2. Hybridoma cells having the capability of producing an antibody that binds specifically to the human FLT3/FLK2 receptor protein, said cells being deposited on Dec. 19, 1995 under No. DSM ACC2248 at the German Collection of Microorganisms and Cell Cultures Ltd., DSMZ, in accordance with the Budapest Treaty and designated BV10A4H2.

* * * * *